US011241361B2

(12) United States Patent
Deutschle (10) Patent No.: US 11,241,361 B2
(45) Date of Patent: Feb. 8, 2022

(54) HOLDING DEVICE FOR THE FLEXIBLE TREATMENT OF PHARMACEUTICAL PACKAGING MATERIALS

(71) Applicant: Schott AG, Mainz (DE)

(72) Inventor: Gregor Fritz Deutschle, Idstein (DE)

(73) Assignee: Schott AG, Mainz (DE)

( * ) Notice: Subject to any disclaimer, the term of this patent is extended or adjusted under 35 U.S.C. 154(b) by 0 days.

(21) Appl. No.: 17/031,381

(22) Filed: Sep. 24, 2020

(65) Prior Publication Data

US 2021/0085562 A1 Mar. 25, 2021

(30) Foreign Application Priority Data

Sep. 25, 2019 (EP) ...................................... 19199683

(51) Int. Cl.
  *A61J 1/16* (2006.01)
  *A61J 1/06* (2006.01)
  *A61J 1/14* (2006.01)
  *A61M 5/00* (2006.01)

(52) U.S. Cl.
  CPC . *A61J 1/16* (2013.01); *A61J 1/06* (2013.01); *A61J 1/1412* (2013.01); *A61M 5/002* (2013.01)

(58) Field of Classification Search
  CPC .. A61J 1/16; A61J 1/06; A61J 1/1412; A61M 5/002; A61M 5/008
  USPC .................................................. 206/364, 370
  See application file for complete search history.

(56) References Cited

U.S. PATENT DOCUMENTS

| 2005/0133386 | A1 | 6/2005 | Wong | |
| 2012/0248057 | A1 | 10/2012 | Bogle et al. | |
| 2015/0108034 | A1* | 4/2015 | Deutschle | A61J 1/16 206/562 |
| 2017/0197745 | A1* | 7/2017 | Deutschle | B65B 1/46 |
| 2019/0135462 | A1 | 5/2019 | Broadbent et al. | |
| 2021/0009320 | A1* | 1/2021 | Clavel | A61J 1/14 |
| 2021/0069060 | A1* | 3/2021 | Kloke | A61M 5/008 |
| 2021/0220221 | A1* | 7/2021 | Komann | A61M 5/20 |

FOREIGN PATENT DOCUMENTS

| DE | 10 2012 110 339 A1 | 11/2013 |
| WO | 2015/023924 A1 | 2/2015 |

OTHER PUBLICATIONS

European Office Action dated Feb. 28, 2020 for European Patent Application No. 19 199 683.4 (7 pages).

* cited by examiner

*Primary Examiner* — Jacob K Ackun
(74) *Attorney, Agent, or Firm* — Taylor IP, P.C.

(57) ABSTRACT

A container holding device for holding one or more containers includes: a base plate having an upper surface, a bottom surface, and one or more holes each extending from the upper surface to the bottom surface and having a central symmetry axis $L_{axis}$ orthogonal to the base plate; and two or more holding elements that are located around each hole beneath the bottom surface of the base plate. The holding elements are configured to: contact an outer surface of a container that is placed into the container holding device at a bottom edge of a top region of the container, such that the container hangs in the container holding device in a first position p1 in which the holding elements do not exert any force on the outer surface of the container that is radial; and contact the outer surface of the container in a shoulder region.

20 Claims, 7 Drawing Sheets

HOLDING DEVICE FOR THE FLEXIBLE TREATMENT OF PHARMACEUTICAL PACKAGING MATERIALS

CROSS REFERENCE TO RELATED APPLICATIONS

This application claims priority to European Patent Application EP 19199683.4, filed on Sep. 25, 2019, which is incorporated in its entirety herein by reference.

BACKGROUND OF THE INVENTION

1. Field of the Invention

The present invention relates to a container holding device for holding a plurality of containers, each container including a top region, a neck region, a shoulder region and a body region, wherein the holding device includes a base plate and holding elements which may be in the form of clips. The invention also relates to a kit including a container holding device and a closure system holding device, to a process for producing closed containers and to the use of a holding device.

2. Description of the Related Art

In the processing of containers for use in pharmaceutical or medical applications, generally so-called nested solutions are preferred nowadays, where a holding device for containers (also called a "nest") is used for concurrently holding or supporting a plurality of containers in a given configuration. The nests are usually delivered to a customer, such as a pharmaceutical company or filler, sterile packaged in a transport or packaging container (also called a "tub"). For further processing the containers, the tubs are opened under sterile conditions, e.g. in a clean room. Further processing takes place either with the nest still accommodated in the tub, or after removal of the nest of the tub. Further processing the containers may include a step of filling the containers with a substance, e.g. a pharmaceutical composition, in liquid form and sealing the pre-filled containers with stoppers, plungers or the like. After the further processing, the containers may be sterile packaged again in a tub, for delivery to final customers.

With the so-called clip nests, necked containers are held at the rolled edge, i.e. at the widened upper rims adjacent narrow neck portions, by resilient holding arms, such as clips. The bodies and bottoms of the vials are freely accessible, which may be required for further processing, such as freeze-drying (lyophilization). An example of such a holding device known from the prior art are the nests disclosed, for example, in FIG. 2f of DE 10 2012 110 339 A1. These nests comprise a base plate comprising holes in a defined array, wherein at the upper side of the base plate resilient retaining tongues are arranged around each hole. The containers are hanging in the holes of the nests and are held in position by the tongues that are located beneath the rolled edge or the containers. To close the containers after they have been filled with a pharmaceutical composition and/or after the have been treated, for example, by lyophilization, in a sterile pharmaceutical filling machine, the base plate is moved downwards (or, if the containers are standing on a substrate such as a table of the pharmaceutical filling machine, the containers are moved upwards by raising the table) the containers are closed at the top side. Closing is usually accomplished by pressing a stopper in the open end of the containers, followed by sealing the rolled edge of the containers by a cap. This process can also be simplified by using one-part closure systems such as the RayDyLyo® closure system (ARaymondlife SASU, France), which comprise a combination of the stopper and the cap.

Usually, closing the containers in the container nest is accomplished by applying a further nest (cap nest) that comprises the closure systems in an arrangement that corresponds to the arrangement of the containers in the container nest. To close the containers, the two nests are pressed against each other. In the case of the nests disclosed in FIG. 2f of DE 10 2012 110 339 A1, in order to remove the filled containers from the container nest, the first step is to pull the cap nest upwards and the second step is to pull the containers out of the vial nest upwards.

The above described nests may also be suitable for weighing the containers in the nest. For weighing, the container is also lifted within the clip receptacles to create enough space for the weighing process. However, if the vials are touched by the tongues, the weighing result may be affected. Therefore, as much free space as possible must be created. Since these steps with today's nests require very high precision, which can often only be guaranteed by the use of robots, the vials are usually removed from the nest for the weighing and closing steps. Removal of the containers out of the nest, however, places certain demands on the dimensional design of the nest.

Since the diameter of the holes in the nest disclosed in DE 10 2012 110 339 A1 is at least equal to the outer diameter of the containers in the body region and as sufficient free space must still remain around the holes for positioning the clips at the upper surface of the base plate, these prior art nests are subjected to certain restrictions with regard to the density in which the containers can be arranged within the nest. Furthermore, removal of the filled and sealed containers from the nest in the separate process steps of removing the cap nest and removing the containers from the container nest can still be simplified in order to improve the process economy.

Moreover, containers nests such as those disclosed in DE 10 2012 110 339 A1 are, to a certain extent, disadvantageous for bigger containers having an outer diameter of 40 mm or even larger if these containers, as stated above, have to be raised within the nest to apply the closure systems or have to be removed out of the nest for certain process steps. As the tongues are holding the containers beneath the rolled edge, they must grip with the diameter of that edge. Furthermore, the nest must have an opening with at least the body diameter of the container so that the container can be lifted out of the nest. As the ratio of the diameter of the rolled edge to the diameter of the body region determines the size of the tongues and as the tongues must bridge the difference in diameter in order to hold the vials reliably in the nest, diameter ratios that deviate from the standard, such as particularly large vials, require very large holding elements, as the crimp diameters usually do not exceed 20 mm, but the body diameters can reach values up to 40 mm (50R) or 47 mm (100R).

What is needed in the art is a way to at least partly overcome a disadvantage arising from the prior art.

SUMMARY OF THE INVENTION

Exemplary embodiments provided according to the present invention provide a container nest, such as a vial nest, which holds containers, such as vials, in a larger density compared to the container nests known from the prior art.

Exemplary embodiments provided according to the present invention also provide a container nest, such as a vial nest, which helps to increase the process economy in a pharmaceutical filling station, particularly when it comes to the step of removing the closed containers, which may be closed vials, out of the container nest. Exemplary embodiments provided according to the present invention also provide a container nest, such as a vial nest, which allows an easy removal of containers out of the nest not only for common DIN-ISO vials such as 2R- or 4R-vials, but also of larger vials such as 50R- or 100R-vials. Exemplary embodiments provided according to the present invention also provide a nest, which allows for the accommodation of closure systems and/or vials with different dimensions, particularly dimension not according to DIN-ISO, such as to provide a nest, which allows for the accommodation of closure systems with custom dimensions and/or custom vial sizes.

In some exemplary embodiments provided according to the present invention, a container holding device for holding one or more containers includes: a base plate having an upper surface and a bottom surface, the base plate including one or more holes, each hole extending from the upper surface to the bottom surface and having a central symmetry axis $L_{axis}$ orthogonal to the base plate; and two or more holding elements that are located around each hole beneath the bottom surface of the base plate. The holding elements are configured to: contact an outer surface of a container that is placed into the container holding device at a bottom edge of a top region of the container, such that the container hangs in the container holding device in a first position p1 in which the holding elements do not exert any force on the outer surface of the container that is, with respect to the central symmetry axis $L_{axis}$, radial; and contact the outer surface of the container in a shoulder region of the container, thereby stabilizing the container if the container is raised upwards in the container holding device towards a second position p2.

In some exemplary embodiments provided according to the present invention, a kit includes: a container holding device including: a base plate having an upper surface and a bottom surface, the base plate including one or more holes, each hole extending from the upper surface to the bottom surface and having a central symmetry axis $L_{axis}$ orthogonal to the base plate; and two or more holding elements that are located around each hole beneath the bottom surface of the base plate; the holding elements are configured to: contact an outer surface of a container that is placed into the container holding device at a bottom edge of a top region of the container, such that the container hangs in the container holding device in a first position p1 in which the holding elements do not exert any force on the outer surface of the container that is, with respect to the central symmetry axis $L_{axis}$, radial; and contact the outer surface of the container in a shoulder region of the container, thereby stabilizing the container if the container is raised upwards in the container holding device towards a second position p2; one or more containers held by the container holding device; and a closure system holding device that holds one or more closure systems. An arrangement of the closure systems in the closure system holding device corresponds to an arrangement of the one or more containers in the container holding device.

In some exemplary embodiments provided according to the present invention, a process for producing closed containers includes: providing a container holding device, one or more containers having an opening at a top edge of a top region hanging in a first position p1 in the container holding device, the container holding device including: a base plate having an upper surface and a bottom surface, the base plate including one or more holes, each hole extending from the upper surface to the bottom surface and having a central symmetry axis $L_{axis}$ orthogonal to the base plate; and two or more holding elements that are located around each hole beneath the bottom surface of the base plate; the holding elements being configured to: contact an outer surface of the one or more containers that is placed into the container holding device at a bottom edge of the top region of the container, such that the container hangs in the container holding device in the first position p1 in which the holding elements do not exert any force on the outer surface of the container that is, with respect to the central symmetry axis $L_{axis}$, radial; and contact the outer surface of the container in a shoulder region of the container, thereby stabilizing the container if the container is raised upwards in the container holding device towards a second position p2; bringing one or more of the containers from the first position p1 into the second position p2; and imposing the top region of the container with a closure system including a closure cap and an integrated flexible stopper.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Exemplary embodiments provided according to the present invention provide a container holding device for holding one or more containers, each container including a top region with a top edge, a bottom edge and an outer diameter d1, a neck region having an outer diameter d2<d1, a shoulder region, and a body region with an outer diameter d3>d1. The container holding device includes: a base plate having an upper surface and a bottom surface, the base plate including one or more holes, each hole extending from the upper surface to the bottom surface and having a central symmetry axis $L_{axis}$ orthogonal to the base plate; and two or more holding elements that are located around each hole beneath the bottom surface of the base plate. The holding elements are configured to: contact the outer surface of a container that is placed into the container holding device at the bottom edge of the top region, such that the container is hanging in the container holding device in a first position p1 in which the holding elements do not exert any force on the outer surface of the container that is, with respect to the central symmetry axis $L_{axis}$, radial; and contact the outer surface of the container in the shoulder region of the container, thereby stabilizing the container if the container is raised upwards in the container holding device towards second position p2.

In the container holding device provided according to the present invention, the bottom surface of the base plate is the surface that, if containers are hanging in the holding device in position p1, is facing towards the top region of the container, which may be in the form of a rolled edge. Furthermore, the expression "the holding elements do not exert any force on the outer surface of the container that is, with respect to said central symmetry axis $L_{axis}$, radial" may be understood in such a way that the holding elements do not press against the outer surface of the neck region of a container that is hanging in the holding device in position p1, but that the holding elements simply contact the outer surface of the container at the bottom edge of the top region, i.e. they may contact the container at the underside of the rolled edge. Accordingly, the holding elements may be configured such that they do not increase the force that is necessary to move the container from position p1 to position p2. The holding elements may be adapted to the containers so that containers with a rolled edge rest loosely with the bottom side of the rolled edge on the holding elements.

In some embodiments, the container is a pharmaceutical container that is rotationally symmetrical around a longitudinal axis of the container and that has at least one opening at the top edge of the container.

In some embodiments, the container is selected from the group consisting of a vial, a vartridge, an ampule, a cartridge or a syringe.

In some embodiments, the container is a vial, such as a vial in which the top region has the shape of a rolled edge. The container holding device according to the present invention may thus be a holding device for vials, i.e. a vial nest.

In some embodiments, holes are arranged in a regular arrangement of rows and columns distributed on the base plate, with the rows and columns arranged regularly offset from each other and forming a recurring arrangement. This regular arrangement is advantageous for automated treatment of the containers.

In some embodiments, the holding elements are arranged along a circle around each hole.

In some embodiments, two, three, four or more holding elements are arranged along a circle around each hole. In some embodiments, three or four holding elements are arranged at regular intervals along a circle around the individual holes on the underside of the base plate.

In some embodiments, the holding elements are designed in the form of clip.

In some embodiments, each clip includes a first region that is configured to contact the outer surface of the container at the bottom edge of the top region if the container is hanging in the first position p1; and a second region that is configured to contact the outer surface of the container in the shoulder region of the container if the container is stabilized in the second position p2.

In some embodiments, the clips are in the form of a flexible holding arm. The flexible holding arm may include a holding nose that is located at the bottom part of the flexible holding arm and that is configured to hold a container at the bottom edge of the top region, i.e. beneath the rolled edge.

In some embodiments, the clips are arranged obliquely below the base plate so that the clips, when an object that has the same diameter or almost the same diameter as the hole is introduced into the hole from the upper surface of the base plate, are pushed away from the central symmetry axis $L_{axis}$ of the holes by the approaching object.

In some embodiments, the clips include a substantially planar inner surface that is directed towards the central symmetry axis $L_{axis}$ of the holes, wherein a straight line that is tangentially applied to the inner surface and that runs in the same plane as the central symmetry axis $L_{axis}$ of the holes includes an angle α with the central symmetry axis $L_{axis}$ of the holes.

In some embodiments, α is in the range from 1 to 45 degree, such as in the range from 1 to 30 degrees, 1.5 to 20 degrees, 1.5 to 15 degrees, or in the range from 2 to 5 degrees.

In some embodiments, the holes have a diameter d4=d3 or d4<d3. In some embodiments of the container holding device provided according to the present invention—contrary to the nests disclosed in DE 10 2012 110 339 A1—the diameter of the holes in the base plate is smaller than the diameter of the body region of the containers that can be held in the container holding device. As a consequence, a higher density in which the containers are held in the container holding device can be achieved.

In some embodiments, the following condition is fulfilled: d4<0.99×d3; such as d4<0.97×d3, d4<0.95×d3, or d4<0.93×d3.

In some embodiments, the holes have a diameter d4>d1. In some embodiments of the container holding device provided according to the present invention, the diameter of the holes in the base plate is larger than the diameter of the top region of the containers that can be held in the container holding device. If the containers are thus lifted from position p1 into position p2, the holding elements can be configured in such a way that the top region of the container, such as the rolled edge of a vial, protrudes beyond the upper surface of the base plate so that, for example, it is easier to close the containers with a closure system.

In some embodiments, the following condition is fulfilled: d4<1.25×d1; such as d4<1.2×d1, d4<1.15×d1, d4<1.1×d1, or d4<1.05×d1.

In some embodiments, d4<d3 and the following condition is fulfilled: d4>1.25×d1; such as d4>1.3×d1, d4>1.35×d1, d4>1.4×d1, d4>1.45×d1, d4>1.5×d1, d4>1.55×d1, or d4>1.6×d1.

In some embodiments, the following condition is fulfilled: d1<d4<d3.

In some embodiments, the holding elements are designed as holding elements, which may be in the form of elastic clips, but have sufficient elasticity to be pivoted or folded away when the container holding device is removed from the top region of the containers or when the containers are pulled downward out of the container holding device. This can be easily achieved by suitable dimensioning, material selection and design of the material thickness of the holding elements. The holding elements may therefore be made of a plastic material.

In some embodiments, the plastic material fulfills at least one of the following conditions:
- α) a Young's Modulus in the range from 0.6 to 3.5 GPa, such as in the range from 0.7 to 3 GPa or in the range from 0.8 to 2.7 GPa, determined according to ISO 527-1/-2; and/or
- β) a Shore Hardness in the range from 55 to 90, such as in the range from 60 to 85 or in the range from 65 to 82, determined according to ISO 7619-1.

In some embodiments, the base plate has a width in the range from 150 to 300 cm, such as in the range from 175 to 275 cm or in the range from 200 to 250 cm, and a length in the range from 300 to 450 cm, such as in the range from 325 to 425 cm or in the range from 350 to 400 cm container.

In some embodiments, the container holding device further includes one or more containers that are hanging in position p1.

In some embodiments, the container holding device is a vial nest designated to accommodate vials with a size designation "2R", "3R", or "4R" according to DIN EN ISO 8362-1:2016-06 and the container holding device includes 80 to 140 vials, such as 90 to 120 vials or 100 to 110 vials, that are held in position p1.

In some embodiments, the diameter of the holes in the base plate is in the range from 13 to 20 mm, such as in the range from 15 to 19 mm or in the range from 16 to 18 mm.

In some embodiments, $d4<1.35 \times d1$; such as $d4<1.3 \times d1$.

In some embodiments, $d4<d3$ and $d4>1.4 \times d1$; such as $d4>1.45 \times d1$. In some embodiments, the container holding device is a vial nest designated to accommodate vials with a size designation "6R", "8R", "10R" or "15R" according to DIN EN ISO 8362-1:2016-06 and the container holding device includes 40 to 68 vials, such as 44 to 58 vials or 48 to 56 vials that are held in position p1.

In some embodiments, the diameter of the holes in the base plate is in the range from 20 to 35 mm, such as in the range from 22 to 30 mm or in the range from 24 to 26 mm.

In some embodiments, $d4<1.25 \times d1$, such as $d4<1.2 \times d1$.

In some embodiments, $d4<d3$ and $d4>1.3 \times d1$, such as $d4>1.35 \times d1$.

In some embodiments, the container holding device is a vial nest designated to accommodate vials with a size designation "20R", "25R" or "30R" according to DIN EN ISO 8362-1:2016-06 and the container holding device includes 20 to 38 vials, such as 22 to 36 vials or 24 to 30 vials that are held in position p1.

In some embodiments, the diameter of the holes in the base plate is in the range from 20 to 35 mm, such as in the range from 22 to 30 mm or in the range from 24 to 26 mm.

In some embodiments, $d4<1.25 \times d1$, such as $d4<1.2 \times d1$.

In some embodiments, $d4<d3$ and $d4>1.3 \times d1$, such as $d4>1.35 \times d1$.

In some embodiments, the container holding device is a vial nest designated to accommodate vials with a size designation "50R" according to DIN EN ISO 8362-1:2016-06 and the container holding device includes 10 to 30 vials, such as 12 to 25 vials or 15 to 20 vials that are held in position p1.

In some embodiments, the diameter of the holes in the base plate is in the range from 20 to 35 mm, such as in the range from 22 to 30 mm or in the range from 24 to 26 mm.

In some embodiments, $d4<1.25 \times d1$, such as $d4<1.2 \times d1$.

In some embodiments, $d4<d3$ and $d4>1.3 \times d1$, such as $d4>1.35 \times d1$.

In some embodiments, the container holding device is a vial nest designated to accommodate vials with a size designation "100R" according to DIN EN ISO 8362-1:2016-06 and the container holding device includes 8 to 20 vials, such as 10 to 18 vials or 12 to 15 vials that are held in position p1.

In some embodiments, the diameter of the holes in the base plate is in the range from 20 to 35 mm, such as in the range from 22 to 30 mm or in the range from 24 to 26 mm.

In some embodiments, $d4<1.25 \times d1$, such as $d4<1.2 \times d1$.

In some embodiments, $d4<d3$ and $d4>1.3 \times d1$, such as $d4>1.35 \times d1$.

In some exemplary embodiments provided according to the present invention, a kit includes: the previously described container holding device; and a closure cup holding device that holds one or more closure systems. The arrangement of the closure systems in the closure system holding device corresponds to the arrangement of the containers in the container holding device.

In some embodiments, the closure cup holding device includes a base plate having an upper surface and a bottom surface, and closure system holding elements that are located at the upper surface or the bottom surface of the base plate, the closure system holding elements are configured such that, when the container holding device and the closure system holding device are pressed together in order to close the containers in the container holding device with the closure systems in the closure system holding device, the holding elements of the container holding device are pushed away from the central symmetry axis $L_{axis}$ by the approaching closure system holding elements.

In some embodiments, the closure systems in the closure system holding device have an outer diameter d5 such that, when the container holding device and the closure system holding device are pressed together in order to close the containers in the container holding device with the closure systems in the closure cup holding device, the holding elements of the container holding device are pushed away from the central symmetry axis $L_{axis}$ by the approaching closure system.

In some embodiments, the closure system includes an elastomeric stopper and a closure cap. Such a closure system is, for example, disclosed in US 2012/0248057 A1 or in WO 2015/023924 A1. Also suitable in this context are cap systems such as Daikyo Plascap® and LyoSeal® (West Pharmaceutical Services, Inc., USA) or RayDyLyo® (ARaymondlife SASU, France), arranged in a suitable nest.

In some embodiments, the kit further includes a transport and packaging container that accommodates the container holding device.

In some exemplary embodiments provided according to the present invention, a process for producing closed containers includes:
I) providing a previously described container holding device or kit, with one or more containers having an opening at the top edge of the top region are hanging in position p1 in the container holding device;
II) bringing one or more of the containers from position p1 into position p2; and
III) imposing the top region of the container with a closure system.

In some embodiments, the container, before the top region of the container is imposed with the closure system, is closed with a stopper at least a part of which is introduced into the top region of the container.

In some embodiments, in process step III) a closure system is used that includes an elastomeric stopper and a closure cap and, if the top region of the container is imposed with the closure system, at least a part of the elastomeric stopper is introduced into the top region of the container. Suitable cap systems are those that have been described previously in connection with the kit provided according to the present invention.

In some embodiments, the closure system is arranged in a closure system holding device of the kit provided according to the present invention.

In some embodiments, imposing the top region of the container with a closure system in process step III) is accomplished by pressing together the container holding device and the closure system holding device, and the holding elements of the container holding device are pushed away from the central symmetry axis $L_{axis}$ by the approaching closure system and/or by the approaching closure system holding elements.

In some embodiments, the process further includes:
IV) removing the closed container from the container holding device by moving the closed container downwards or by pulling the container holding device upwards.

In some exemplary embodiments provided according to the present invention, a use of the previously described container holding device for producing closed containers is also provided.

Figure 1A:
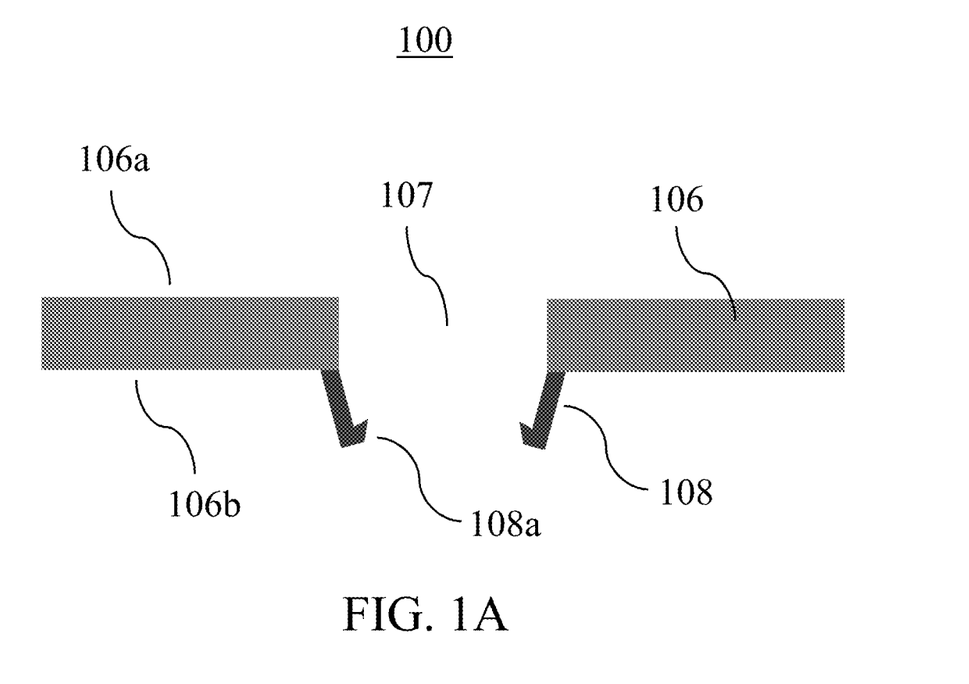
FIG. 1A illustrates a part of a container holding device (the area around a single hole) provided according to the present invention in a cross-sectional side view.
Figure 1B:
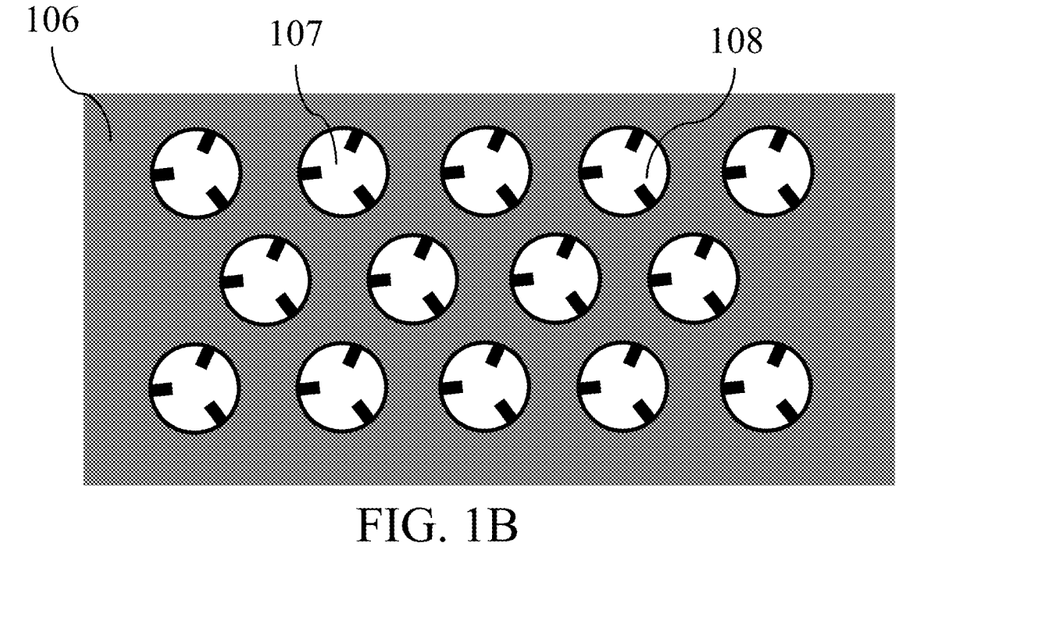
FIG. 1B illustrates in a top view a container holding device provided according to the present invention.
Figure 3:
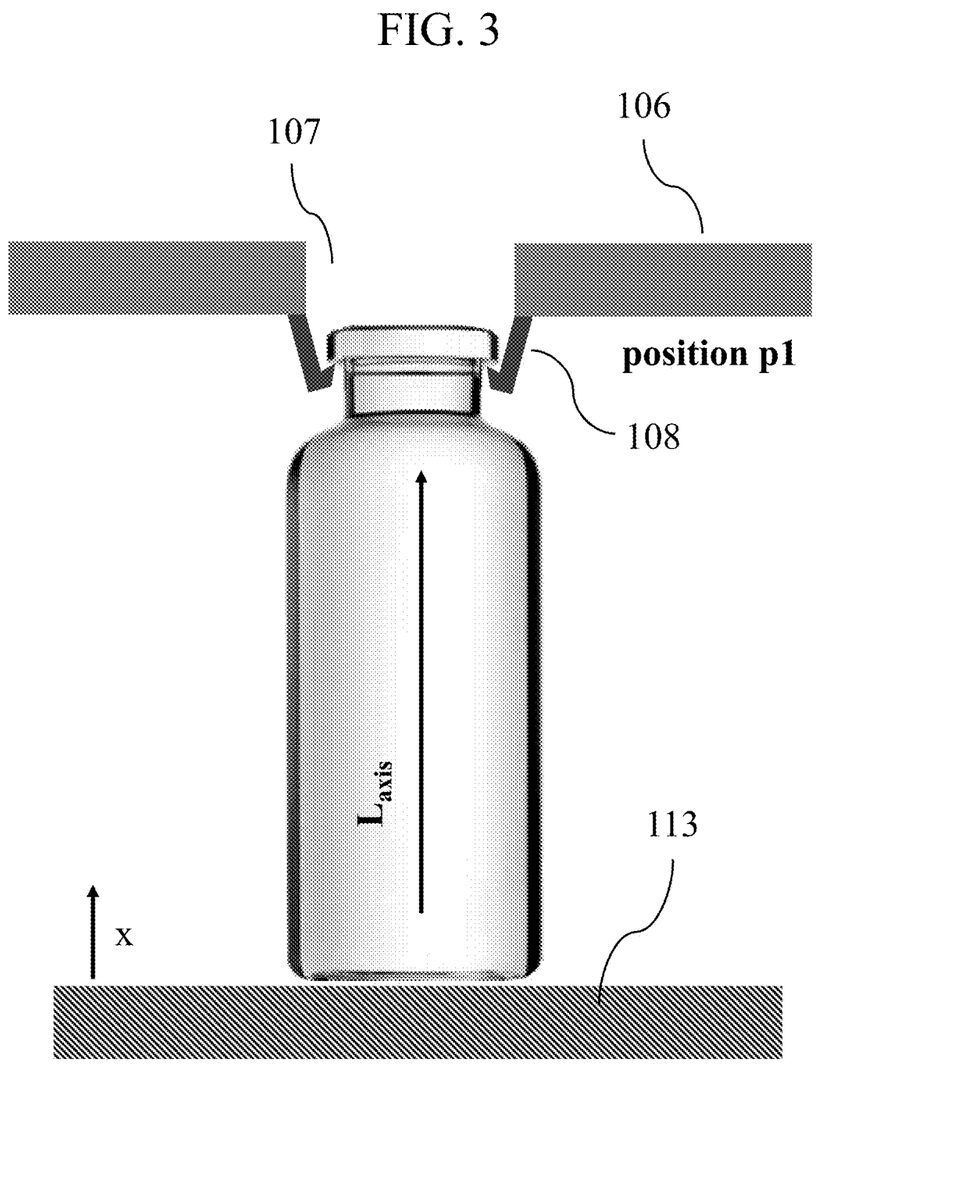
FIG. 3 illustrates in a cross-sectional view the way in which a container is held in position p1 in a container holding device provided according to the present invention.

Referring now to the drawings, FIG. 1 shows a part of a container holding device 100 (i.a. the area around a single hole 107) provided according to the present invention in a cross-sectional side view. As can be seen in FIG. 1A, the container holding device 100 provided according to the present invention includes a base plate 106 having an upper surface 106a and a bottom surface 106b. The base plate 106 includes one or more holes 107, each hole 107 extending from the upper surface 106a to the bottom surface 106b and having a central symmetry axis $L_{axis}$ orthogonal to the base plate 106 (see, for example, FIG. 3). The container holding device 100 further includes two or more holding elements 108 that are located around each hole 107 beneath the bottom surface 106b of the base plate 106. The holding elements of the holding device 100 shown in FIG. 1A are designed in the form of clips. As can be seen in FIG. 1A, one significant difference to the vial nest known from the prior art is that the holding elements 108 are located at the bottom surface 106b of the base plate 106. The vials 101 are thus hanging beneath the base plate 106. As can be seen in FIG. 1B, the holes 107 can be arranged in a regular arrangement of rows and columns distributed on the base plate 106, with the rows and columns being arranged regularly offset from each other and forming a recurring arrangement. This regular arrangement is advantageous for automated treatment of the containers 101. In the device 100 shown in FIG. 1B, three clips 108 can be arranged at regular intervals along a circle around the individual holes 107 on the underside 106b of the base plate 106, but it is also possible to arrange two, four or even more clips 108. The clips 108 shown in FIG. 1A are designed in the form of a flexible holding arm that includes a holding nose 108a that is located at the bottom part of the flexible holding arm and that is configured to hold a container 101 at the bottom edge 102b of the top region 102, i.e. beneath the rolled edge (as shown in FIG. 3).

Figure 2:
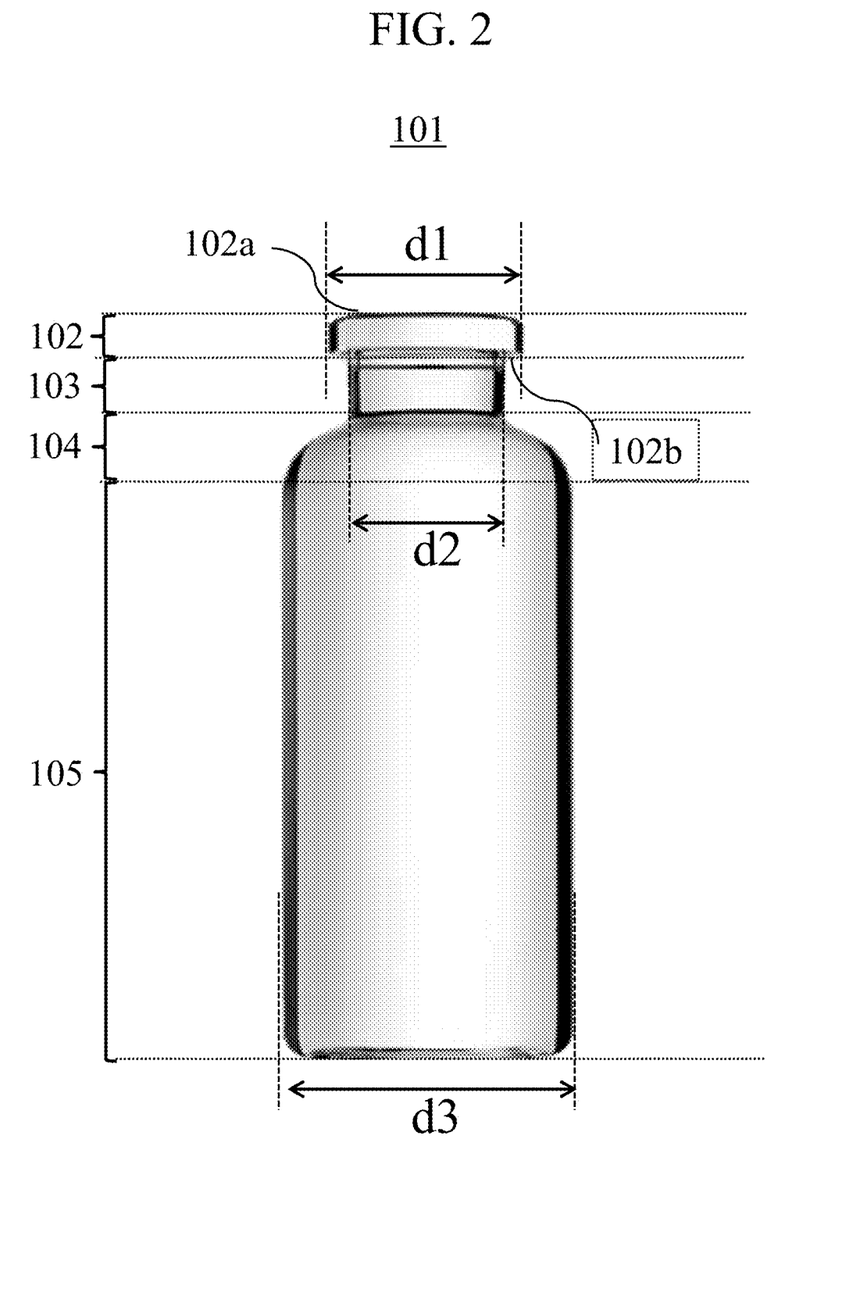
FIG. 2 illustrates in a cross-sectional view the regions of a container that can be held in the container holding device provided according to the present invention.

FIG. 2 shows in a cross-sectional view the regions of a typical container 101 that can be held in the container holding device 100 provided according to the present invention. The container 101 is in the form of a vial. The container 101 includes a top region 102 with a top edge 102a, a bottom edge 102b and an outer diameter d1, a neck region 103 having an outer diameter d2<d1, a shoulder region 104 and a body region 105 with an outer diameter d3>d1. As shown in FIG. 2, the top region 102 of the container 101 may be designed in the form of a rolled edge.

As a material for the container 101 to be held in the container holding device 100 provided according to the present invention, any material can be selected which the person skilled in the art would consider suitable for that purpose. Pharmaceutical containers made from tubular glass are commercially available in a range of different sizes with dimensions according to the DIN EN ISO 8362-1:2016-06 standard. Molded glass vials are commercially available in a range of different sizes with dimensions according to the DIN/ISO 8362-4 standard.

Glass has traditionally been the only choice for container material but problems with glass breakage, delamination, particulates due to glass-on-glass collisions, and stability of some products resulted in development and usage of suitable polymeric materials. One example of such polymeric material is TOPAS® cyclic olefin polymer. Vials made of polymeric materials are commercially available in size ranges and dimensions that typically closely mimic those of glass vials. Polymeric materials are significantly less scratch resistant than glass and existing aseptic processing equipment has not been redesigned to mitigate the risks of scratching. Scratched surfaces of containers are a serious concern for the perceived quality of the product, but also severely limits the inspection of the containers for particulates. Such inspection is typically a regulated requirement for good manufacturing practice. Processing of vials in the container holding device 100 provided according to the present invention is thus an effective solution to prevent scratching of vials such as typically occurs during singulated handling of vials or during simultaneous handling of rows of vials. These devices are particularly well suited for processing of polymeric vials but may be used equally well for processing of glass vials.

Figure 6:
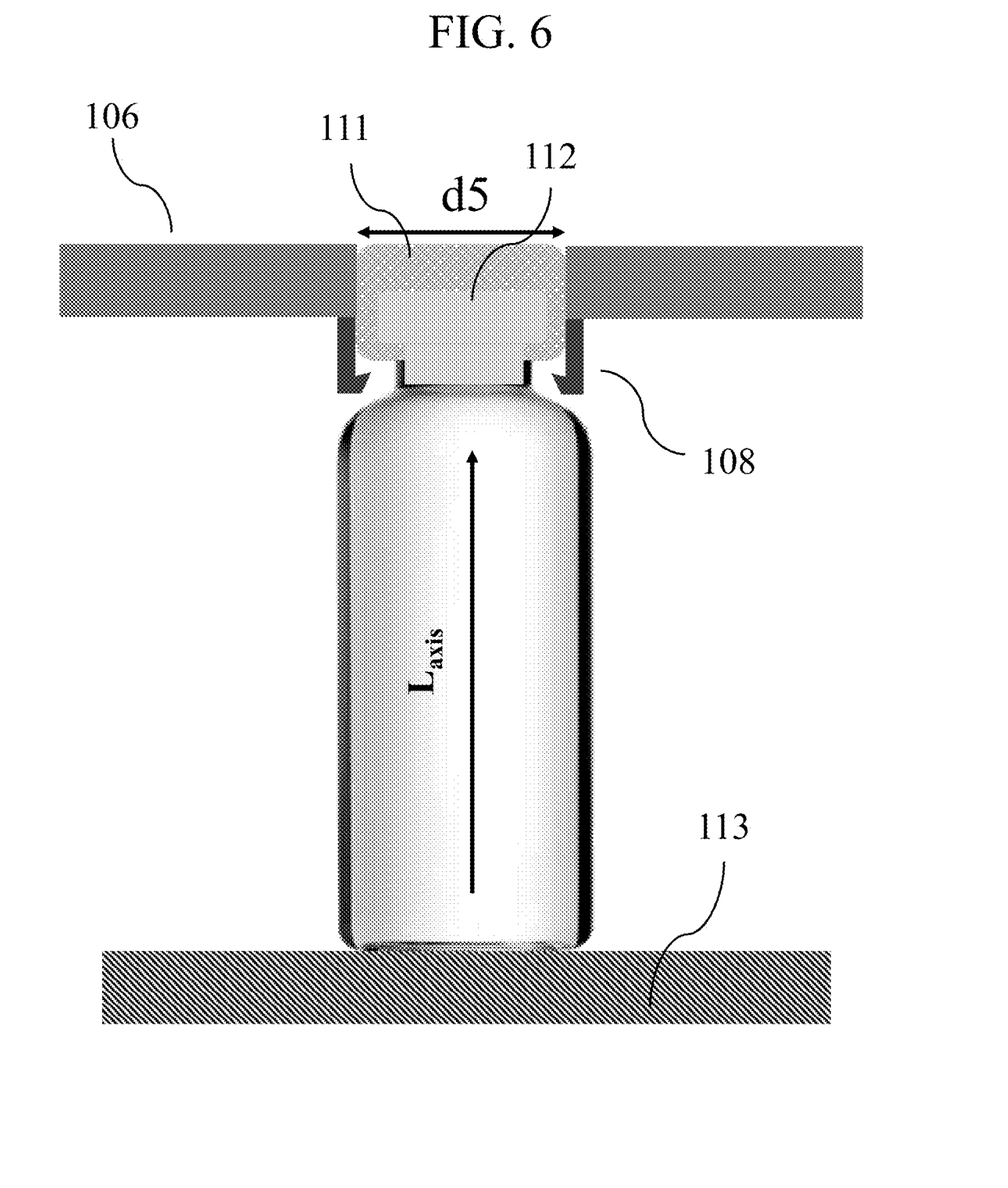
FIG. 6 illustrates in a cross-sectional view how holding elements are pushed away from a central symmetry axis Laxis if a top region of a container is imposed with a closure system having a diameter d5 according to the present invention.

FIG. 3 shows in a cross-sectional view the way in which a container 101 is held in position p1, which may also be referred to as a "first position," in a container holding device 100 provided according to the present invention, whereas FIG. 6 shows in a cross-sectional view the way in which a container 101 is held in position p2, which may also be referred to as a "second position." As can be seen, the holding elements 108 are adapted and arranged to contact the outer surface of a container 101 that is placed into the container holding device 100 at the bottom edge 102b of the top region 102 (in the vial 101 shown in FIG. 3 the holding elements 108 hold the vial 101 below the lower edge of the rolled edge), such that the container is hanging in the container holding device 100 in the first position p1 in which the holding elements 108 do not exert any force on the outer surface of the container 101 that is, with respect to the central symmetry axis $L_{axis}$, radial. The holding elements 108 thus do not press against the outer surface of the neck region 103 of a container 101 and as a consequence the containers 101 rest loosely with the bottom side of the rolled edge laying on the holding elements 108 (to be more precise, with the bottom side 102b of the rolled edge 102 laying on the holding nose 108b of the holding elements 108). Thus, holding elements 108 may be configured in such a way that they do not increase the force that is necessary to move the container from the first position p1 to the second position p2 along the path x (see FIGS. 3 and 4). In the second position p2, the holding elements 108 contact the outer surface of the container 101 in the shoulder region 104 of the container 101, thereby stabilizing the container 101 if the container 101 is raised upwards in the container holding device 100 towards the second position p2. Raising the container 101 from the first position p1 into the second position p2 can, for example, be accomplished by moving the base plate 106 downwards or—as shown in FIGS. 3 and 4—by raising a substrate 113 upwards onto which the containers 101 are placed (such as a table of the pharmaceutical filling machine).

Figure 4:
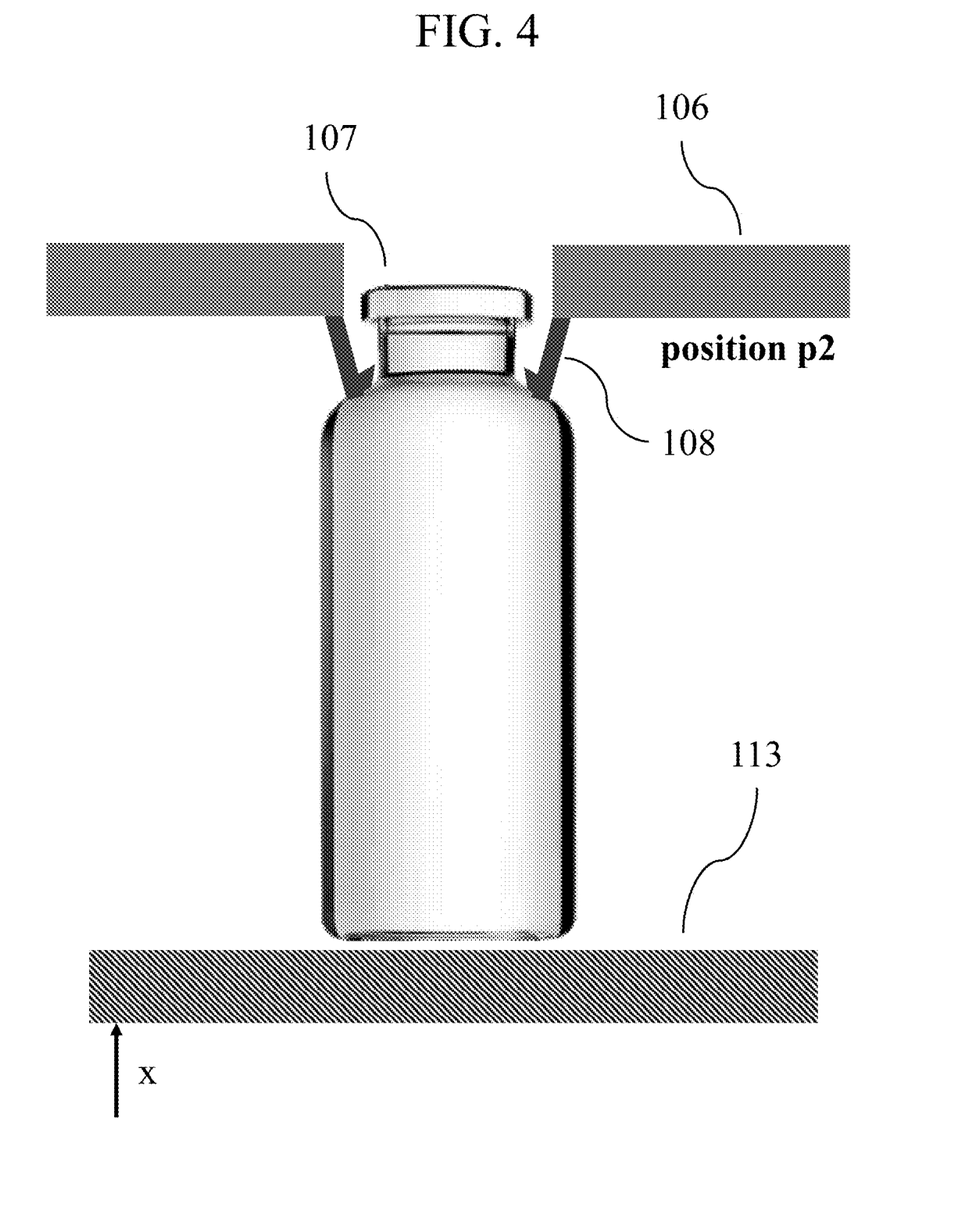
FIG. 4 illustrates in a cross-sectional view the way in which a container is held in position p2 in a container holding device provided according to the present invention.

As can also be seen in FIGS. 3 and 4, the diameter d4 of the holes 107 in the base plate 106 does not have to be as large as the outer diameter d3 of the containers 101 in the body region 105 of the containers as the containers are hanging beneath the base plate 106. However, the diameter d4 of the holes 107 in the base plate 106 may have at least the size of the diameter d1 of the container 101 in the top region (i.e. the diameter of the rolled edge) so that the containers 101 protrude with the top region 102 of the container beyond the upper surface 106a of the base plate 106 when they are lifted from position p1 into position p2. This facilitates imposing the top region 102 of the containers 101 with a closure system.

Figure 5:
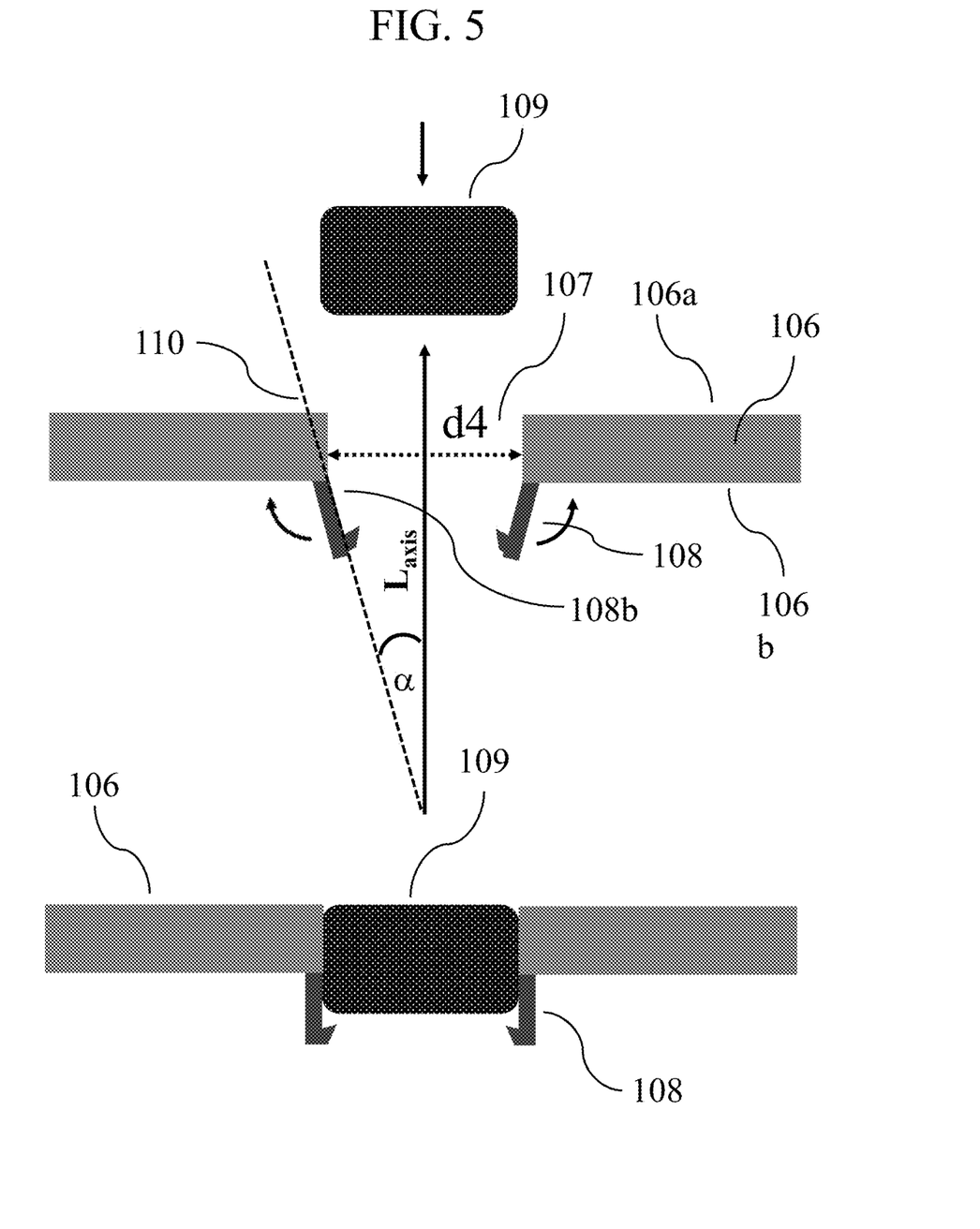
FIG. 5 illustrates an advantage of an inclined arrangement of holding elements on an underside of a base plate provided according to the present invention.

FIG. 5 shows the advantage of an inclined arrangement of the holding elements 108 on the underside 106b of the base plate 106. As shown in FIG. 5, the holding elements 108, which again are designed in the form of clips 108, are arranged obliquely below the base plate 106 so that the clips 108, when an object 109 that has the same diameter or almost the same diameter as the hole 107, such as a closure system (see FIG. 6) or the holding elements of a closure system holding device (see FIG. 7), is introduced into the hole 107 from the upper surface 106a of the base plate 106, are pushed away from the central symmetry axis $L_{axis}$ of the holes 107 by the approaching object 109. Such an arrangement can be realized by clips 108 that include a substantially planar inner surface 108b that is directed towards the central symmetry axis $L_{axis}$ of the holes 107, where a straight line 110 that is tangentially applied to the inner surface 108b and that runs in the same plane as the central symmetry axis $L_{axis}$ of the holes 107 includes an angle α with the central symmetry axis $L_{axis}$ of the holes 107. Pushing away the clips 108 from the central symmetry axis $L_{axis}$ of the holes 107 facilitates pulling the containers 101 downwards out of the container holding device 101 or pulling the container holding device 100 upwards, for example after closing the containers 101 with a closure system.

Figure 7:
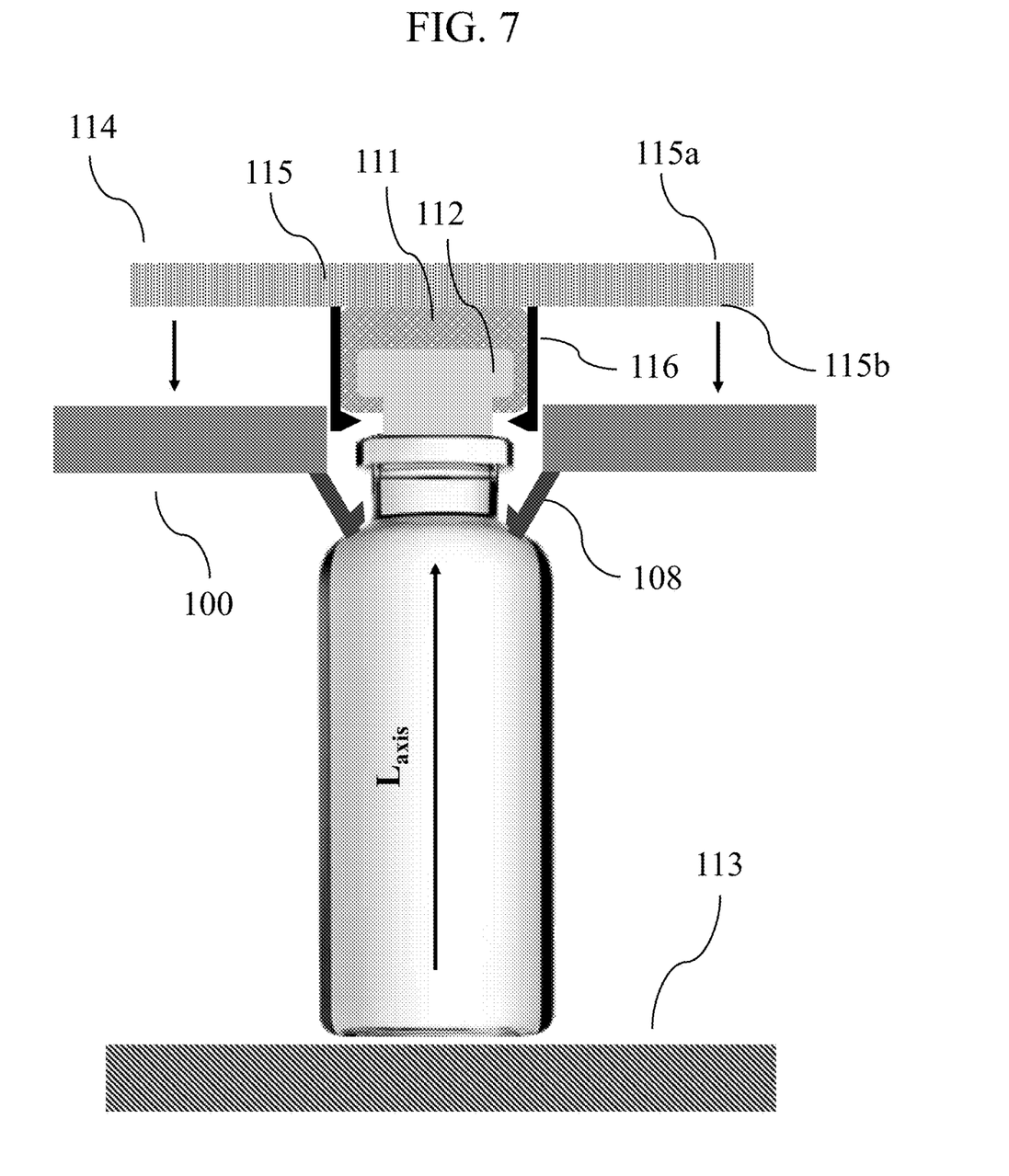
FIG. 7 illustrates in a cross-sectional view how containers in a container holding device provided according to the present invention can be closed with closure systems that are held in a closure system holding device.

FIG. 6 shows in a cross-sectional view how the holding elements 108 are pushed away from the central symmetry axis $L_{axis}$ if the top region 102 of the container 101 is imposed with closure system having a diameter d5. In some embodiments, the closure systems are present in the form of a closure system holding device 114 as shown in FIG. 7. As the diameter of the closure system shown in FIG. 6 is larger than the distance of the clips 108 immediately beneath the base plate 106, the holding elements 108 of the container holding device 100 are pushed away from the central symmetry axis $L_{axis}$ by the approaching closure system. As also shown in FIG. 6, the closure system may comprise a closure cap 111 and a flexible integrated stopper 112. A part of the flexible stopper 112 is introduced into the top region 102 of the container 101 in order to close the container 101 at the open end.

FIG. 7 shows in a cross-sectional view how the containers 101 in a container holding device 100 provided according to the present invention can be closed with closure systems that are held in a closure system holding device 114. As can be seen in FIG. 7, the closure system holding device 114 comprises a base plate 115 having an upper surface 115a and a bottom surface 115b, and closure system holding elements 116 that are located at the bottom surface 115b of the base plate 115 and that also may be designed in the form of flexible holding arms. The closure system holding elements 116 are configured so that, when the container holding device 100 and the closure system holding device 114 are pressed together (i.e. if the closure system holding device 114 is moved downwards in the direction of the two arrows shown in FIG. 7) in order to close the containers 101 in the container holding device 100 with the closure systems in the closure system holding device 114, the holding elements 108 of the container holding device 100 are pushed away from the central symmetry axis $L_{axis}$ by the approaching closure system holding elements 116 (not shown in FIG. 7). Pushing away the clips 108 from the central symmetry axis $L_{axis}$ of the holes 107 facilitates pulling the container holding device 100 upwards after closing the containers 101 with the closure system, where both nests (i.e. the container holding device 100 and the closure system holding device 114) can simultaneously be pulled away to the same side.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS

100 Container holding device
101 container, such as a vial
102 top region of the container 101, such as in the form of a rolled edge
102a top edge of the top region 102
102b bottom edge of the top region 102
103 neck region of the container 101
104 shoulder region of the container 101
105 body region of the container 101
106 base plate
106a upper surface of the base plate 106
106b bottom surface of the base plate 106
107 hole
108 holding elements, such as in the form of clips
108a holding nose located at the lower portion of the clips
108b inner surface of the clips 108
109 object
110 straight line that is tangentially applied to the inner surface 108b
111 closure cap
112 flexible stopper
113 substrate
114 closure system holding device
115 base plate of the closure system holding device 114
115a upper surface of the base plate 115
115b bottom surface of the base plate 115
116 closure system holding elements

What is claimed is:

1. A container holding device for holding one or more containers, the container holding device comprising:
   a base plate having an upper surface and a bottom surface, the base plate comprising one or more holes, each hole extending from the upper surface to the bottom surface and having a central symmetry axis $L_{axis}$ orthogonal to the base plate; and
   two or more holding elements that are located around each hole beneath the bottom surface of the base plate; the holding elements being configured to:
   i) contact an outer surface of a container that is placed into the container holding device at a bottom edge of a top region of the container, such that the container hangs in the container holding device in a first position p1 in which the holding elements do not exert any force on the outer surface of the container that is, with respect to the central symmetry axis $L_{axis}$, radial; and
   ii) contact the outer surface of the container in a shoulder region of the container, thereby stabilizing the container if the container is raised upwards in the container holding device towards a second position p2.

2. The container holding device of claim 1, wherein at least two holding elements are arranged along a circle around each hole.

3. The container holding device of claim 1, wherein the holding elements are designed in the form of clips that are arranged obliquely below the base plate so that the clips, when an object that has a same or almost the same diameter as the hole is introduced into the hole from the upper surface of the base plate, are pushed away from the central symmetry axis $L_{axis}$ of the holes by the introduced object.

4. The container holding device of claim 3, wherein the clips comprise a substantially planar inner surface that is directed towards the central symmetry axis $L_{axis}$ of the holes, wherein a straight line that is tangentially applied to the inner surface and that runs in a same plane as the central symmetry axis $L_{axis}$ of the holes includes an angle α with the central symmetry axis $L_{axis}$ of the holes.

5. The container of claim 4, wherein a is in a range from 1 to 45 degrees.

6. The container of claim 5, wherein a is in a range from 1.5 to 20 degrees.

7. The container holding device of claim 1, further comprising one or more containers that are hanging in the first position p1.

8. The container holding device of claim 1, further comprising one or more containers held by the container holding device, each container comprising a top region with a top edge, a bottom edge and an outer diameter d1, a neck region having an outer diameter d2<d1, a shoulder region, and a body region with an outer diameter d3>d1.

9. The container holding device of claim 8, wherein the one or more containers is selected from a group consisting of a vial, a vartridge, an ampule, a cartridge, and a syringe.

10. The container holding device of claim 8, wherein the holes have a diameter d4<d3.

11. The container holding device of claim 10, wherein the diameter d4<0.95×d3.

12. The container holding device of claim 10, wherein d4>1.25×d1.

13. The container holding device of claim 10, wherein d1<d4<d3.

14. The container holding device of claim 8, wherein the holes have a diameter d4>d1.

15. The container holding device of claim 14, wherein the diameter d4<1.25×d1.

16. The container holding device of claim 8, wherein at least one of the one or more containers protrudes with the top region beyond the upper surface of the base plate when the at least one container is raised from the first position p1 into the second position p2.

17. A kit, comprising:
   a container holding device, comprising:
      a base plate having an upper surface and a bottom surface, the base plate comprising one or more holes, each hole extending from the upper surface to the bottom surface and having a central symmetry axis $L_{axis}$ orthogonal to the base plate; and
      two or more holding elements that are located around each hole beneath the bottom surface of the base plate; the holding elements being configured to:
         contact an outer surface of a container that is placed into the container holding device at a bottom edge of a top region of the container, such that the container hangs in the container holding device in a first position p1 in which the holding elements do not exert any force on the outer surface of the container that is, with respect to the central symmetry axis $L_{axis}$, radial; and
         contact the outer surface of the container in a shoulder region of the container, thereby stabilizing the container if the container is raised upwards in the container holding device towards a second position p2;
   one or more containers held by the container holding device; and
   a closure system holding device that holds one or more closure systems, wherein an arrangement of the closure systems in the closure system holding device corresponds to an arrangement of the one or more containers in the container holding device.

18. The kit of claim 17, wherein the one or more closure systems comprises a closure cap and an integrated flexible stopper.

19. The kit of claim 17, wherein the closure system holding device comprises a base plate having an upper surface and a bottom surface, and closure system holding elements that are located at the top surface or the bottom surface of the base plate, the closure system holding elements being configured such that, when the container holding device and the closure system holding device are pressed together in order to close the one or more containers in the container holding device with the one or more closure systems in the closure system holding device, the holding elements of the container holding device are pushed away from the central symmetry axis $L_{axis}$ by the approaching closure system holding elements.

20. A process for producing closed containers, the process comprising:
   I) providing a container holding device, wherein one or more containers having an opening at a top edge of a top region is hanging in a first position p1 in the container holding device, the container holding device comprising:
      a base plate having an upper surface and a bottom surface, the base plate comprising one or more holes, each hole extending from the upper surface to the bottom surface and having a central symmetry axis $L_{axis}$ orthogonal to the base plate; and
      two or more holding elements that are located around each hole beneath the bottom surface of the base plate; the holding elements being configured to:

contact an outer surface of the one or more containers that is placed into the container holding device at a bottom edge of the top region of the container, such that the container hangs in the container holding device in the first position p1 in which the holding elements do not exert any force on the outer surface of the container that is, with respect to the central symmetry axis $L_{axis}$, radial; and contact the outer surface of the container in a shoulder region of the container, thereby stabilizing the container if the container is raised upwards in the container holding device towards a second position p2;

II) bringing one or more of the containers from the first position p1 into the second position p2; and III) imposing the top region of the container with a closure system comprising a closure cap and an integrated flexible stopper.

\* \* \* \* \*

UNITED STATES PATENT AND TRADEMARK OFFICE
CERTIFICATE OF CORRECTION

PATENT NO. : 11,241,361 B2
APPLICATION NO. : 17/031381
DATED : February 8, 2022
INVENTOR(S) : Gregor Fritz Deutschle

Page 1 of 1

It is certified that error appears in the above-identified patent and that said Letters Patent is hereby corrected as shown below:

In the Claims

Column 13
At Line 40, in Claim 5, please delete "wherein a", and substitute therefore --wherein α--; and
At Line 42, in Claim 6, please delete "wherein a", and substitute therefore --wherein α--.

Signed and Sealed this
Twenty-eighth Day of February, 2023

Katherine Kelly Vidal
*Director of the United States Patent and Trademark Office*